(12) United States Patent
Hagiya et al.

(10) Patent No.: US 7,632,664 B2
(45) Date of Patent: Dec. 15, 2009

(54) METHOD FOR PRODUCING 2-HYDROXY-4-(METHYLTHIO)BUTYRIC ACID

(75) Inventors: Koji Hagiya, Ibaraki (JP); Hiroyuki Asako, Toyonaka (JP)

(73) Assignee: Sumitomo Chemical Company, Limited, Tokyo (JP)

(*) Notice: Subject to any disclaimer, the term of this patent is extended or adjusted under 35 U.S.C. 154(b) by 201 days.

(21) Appl. No.: 11/665,070

(22) PCT Filed: Oct. 13, 2005

(86) PCT No.: PCT/JP2005/019259
§ 371 (c)(1), (2), (4) Date: Apr. 11, 2007

(87) PCT Pub. No.: WO2006/041209
PCT Pub. Date: Apr. 20, 2006

(65) Prior Publication Data
US 2009/0053781 A1  Feb. 26, 2009

(51) Int. Cl.
C12P 13/12 (2006.01)
C12P 11/00 (2006.01)

(52) U.S. Cl. .................... 435/113; 435/130

(58) Field of Classification Search .......... None
See application file for complete search history.

(56) References Cited

U.S. PATENT DOCUMENTS

| 4,524,077 A | 6/1985 | Ruest et al. |
| 4,897,498 A | 1/1990 | Monnier et al. |
| 4,950,773 A | 8/1990 | Monnier et al. |
| 5,250,743 A | 10/1993 | Boaz |
| 5,811,601 A | 9/1998 | Remans et al. |

FOREIGN PATENT DOCUMENTS

| EP | 0 338 735 A1 | 10/1989 |
| EP | 1 260 500 A1 | 11/2002 |
| EP | 1 473 275 A1 | 11/2004 |
| JP | 2001-054380 | 2/2001 |
| WO | WO-03/066524 | 8/2003 |

OTHER PUBLICATIONS

Database WPI, Week 200137, Derwent Publications Ltd., AN—2001-347641, 2 Sheets.
Morrison, R. T. et al., "Study Guide to Organic Chemistry", Fifth Edition, pp. 301-309, 1987.
Steadman, Thomas R. et al., "A Methionine Substitute: 4-Methylthiobutane-1,2-diol", J. Agric Food Chem, vol. 23, No. 6, pp. 1137-1114, 1975.

*Primary Examiner*—Paul A Zucker
(74) *Attorney, Agent, or Firm*—Foley & Lardner LLP

(57) ABSTRACT

A method for producing 2-hydroxy-4-(methylthio)butyric acid which comprises the following steps (A), (B) and (C):

Step (A): step of reacting 1,2-epoxy-3-butene with water to obtain 3-butene-1,2-diol, Step (B): step of reacting 3-butene-1,2-diol with methanethiol to obtain 4-(methylthio)butane-1,2-diol, Step (C): step of oxidizing 4-(methylthio)butane-1,2-diol to obtain 2-hydroxy-4-(methylthio)butyric acid.

12 Claims, No Drawings

METHOD FOR PRODUCING 2-HYDROXY-4-(METHYLTHIO)BUTYRIC ACID

TECHNICAL FIELD

The present invention relates to a method for producing 2-hydroxy-4-(methylthio)butyric acid.

BACKGROUND ART

2-Hydroxy-4-(methylthio)butyric acid is an analog of the essential amino acid 1-methionine, and it is an important compound for using for feed additive. As methods for production thereof, a method comprising adding methanethiol to acrolein to obtain 3-methylthiopropionaldehyde, reacting 3-methylthiopropionaldehyde obtained with hydrogen cyanide to obtain 2-hydroxy-4-methylthiobutyronitrile, and then hydrolyzing 2-hydroxy-4-methylthiobutyronitrile obtained with sulfuric acid has been known (e.g. U.S. Pat. No. 4,524,077).

DISCLOSURE OF THE INVENTION

The present invention provides a method for producing 2-hydroxy-4-(methylthio)butyric acid which comprises the following steps (A), (B) and (C):

Step (A): step of reacting 1,2-epoxy-3-butene with water to obtain 3-butene-1,2-diol, Step (B): step of reacting 3-butene-1,2-diol with methanethiol to obtain 4-(methylthio)butane-1,2-diol, Step (C): step of oxidizing 4-(methylthio)butane-1,2-diol to obtain 2-hydroxy-4-(methylthio)butyric acid.

BEST MODE FOR CARRYING OUT THE PRESENT INVENTION

First, the step (A): step of reacting 1,2-epoxy-3-butene with water to obtain 3-butene-1,2-diol will be illustrated.

1,2-Epoxy-3-butene can be produced, for example, according to known methods such as a method comprising reacting an oxidizing agent such as oxygen, an organic peroxide and hydrogen peroxide with butadiene. As a preferable method, a method comprising reacting butadiene with oxygen in the presence of silver-containing catalyst, for example, described in U.S. Pat. No. 4,897,498.

The reaction of 1,2-epoxy-3-butene and water is preferably conducted in the presence of an acid. Examples of the acid include sulfuric acid; a phosphoric acid compound; a strong acidic ion-exchange resin; a silicate containing at least one element selected from a group 5 element and a group 6 element of the long periodic table as a constituent (hereinafter, simply referred to as the metal-containing silicate); and the like. Among them, the phosphoric acid compound and the metal-containing silicate are preferable.

When sulfuric acid is used as the acid, the reaction may be conducted according to the method described in U.S. Pat. No. 5,250,743. When the strong acidic ion-exchange resin is used as the acid, the reaction may be conducted according to the method described in WO 91/15469.

The cases of using the phosphoric acid compound and the metal-containing silicate will be illustrated below.

First, the case of using the phosphoric acid compound as the acid will be illustrated.

Examples of the phosphoric acid compound include phosphoric acid, phosphorous acid, hypophosphorous acid, metaphosphoric acid and polyphosphoric acid. Commercially available one is usually used. The phosphoric acid compound may be used as an aqueous solution.

The amount of the phosphoric acid compound to be used is usually 0.001 mole or more relative to 1 mole of 1,2-epoxy-3-butene. There is no specific upper limit and it is practically 1 mole or less relative to 1 mole of 1,2-epoxy-3-butene considering economical viewpoint.

The amount of water to be used is usually 1 mole or more relative to 1 mole of 1,2-epoxy-3-butene. There is no specific upper limit and large excess amount thereof, for example, 500 moles relative to 1 mole of 1,2-epoxy-3-butene, may be used also to serve as the solvent.

The reaction of 1,2-epoxy-3-butene and water is usually conducted by mixing 1,2-epoxy-3-butene, water and the phosphoric acid compound in the absence of a solvent or with using water as the solvent. The mixing order is not particularly limited. The reaction may be conducted in the presence of an organic solvent. Examples of the organic solvent include an ether solvent such as diethyl ether, methyl tert-butyl ether and tetrahydrofuran; an ester solvent such as ethyl acetate; a tertiary alcohol solvent such as tert-butanol; and a nitrile solvent such as acetonitrile and propionitrile, and these solvents may be used alone or in a form of a mixture. The amount of the organic solvent to be used is not particularly limited, and it is practically 100 parts by weight or less per 1 part by weight of 1,2-epoxy-3-butene considering volume efficacy.

The reaction is usually conducted under ordinary pressure conditions and may be conducted under reduced pressure conditions or pressurized conditions. The reaction temperature is usually −20 to 100° C., preferably 0 to 100° C.

The progress of the reaction can be confirmed by a conventional analytical means such as gas chromatography, high performance liquid chromatography, thin layer chromatography, nuclear magnetic resonance spectrum analysis and infrared adsorption spectrum analysis.

After completion of the reaction, for example, 3-butene-1,2-diol can be also isolated by adding water and/or a water-insoluble organic solvent to the reaction liquid, if necessary, conducting extraction to obtain an organic layer containing 3-butene-1,2-diol, and concentrating the organic layer as it is or after washing with water or an alkaline water, if necessary. Examples of the water-insoluble organic solvent include a halogenated hydrocarbon solvent such as dichloromethane, chloroform and chlorobenzene; an ether solvent such as diethyl ether and methyl tert-butyl ether; and an ester solvent such as ethyl acetate, and the amount thereof to be used is not particularly limited. Examples of the alkaline water include an ammonia water; an aqueous alkali metal hydrogen carbonate solution such an aqueous sodium hydrogen carbonate solution and an aqueous potassium hydrogen carbonate solution; an alkali metal carbonate such an aqueous sodium carbonate solution and an aqueous potassium carbonate solution; and an aqueous alkali metal hydroxide solution such as an aqueous sodium hydroxide solution and an aqueous potassium hydroxide solution, and the concentration and the amount thereof are not particularly limited.

Next, the case of using the metal-containing silicate as the acid will be illustrated.

In the present invention, the metal-containing silicate is not particularly limited as far as it is a silicate containing the group 5 element of the long periodic table, the group 6 element of the long periodic table or the both elements thereof as a constituent.

Examples of the group 5 element of the long periodic table include vanadium, niobium, tantalum and the like. Examples of the group 6 element of the long periodic table include tungsten, molybdenum, chromium and the like. Preferred are vanadium, molybdenum and tungsten, and more preferred are vanadium and molybdenum.

The metal-containing silicate can be produced, for example, by a method comprising reacting a metal oxide containing at least one element selected from the group 5 element and the group 6 element of the long periodic table as a constituent with a silicon compound in the presence of an organic template, followed by washing or calcining the reaction product obtained as described in EP 1473275 A, Applied Catalysis A: General 179, 11 (1999), J. Chem. Soc., Chem. Commun., 2231 (1995), and the like. Among them, a metal-containing silicate produced by using a metal oxide which is obtained by reacting at least one compound selected from a group 5 metal of the long periodic table, a group 6 metal of the long periodic table, a compound containing the group 5 element of the long periodic table and a compound containing the group 6 element of the long periodic table (hereinafter, simply referred to as the metal or compound) with hydrogen peroxide is preferable as the above-mentioned metal oxide. The method for producing the metal-containing silicate produced by using the metal oxide which is obtained by reacting the metal or compound with hydrogen peroxide will be illustrated below.

Examples of the group 5 metal of the long periodic table include vanadium metal, niobium metal and tantalum metal. Examples of the group 6 metal of the long periodic table include tungsten metal, molybdenum metal and chromium metal. Examples of the compound containing the group 5 element of the long periodic table as a constituent include a vanadium compound such as vanadium oxide, ammonium vanadate, vanadium carbonyl complex, vanadium sulfate and vanadium sulfate ethylene diamine complex; a niobium compound such as niobium oxide, niobium chloride and niobium carbonyl complex; and a tantalum compound such as tantalum oxide and tantalum chloride. Examples of the compound containing the group 6 element of the long periodic table as a constituent include a tungsten compound such as tungsten boride, tungsten carbide, tungsten oxide, ammonium tungstate and tungsten carbonyl complex; a molybdenum compound such as molybdenum boride, molybdenum oxide, molybdenum chloride, molybdenum carbonyl complex; and a chromium compound such as chromium oxide and chromium chloride.

Among the metals or compounds, tungsten metal, the tungsten compound, molybdenum metal, the molybdenum compound, vanadium metal and the vanadium compound are preferable, and molybdenum metal, the molybdenum compound, vanadium metal and the vanadium compound are more preferable.

The metals or compounds may be used alone, or two or more kind thereof may be used. Among the metals or compounds, there are metals or compounds having hydrates and the hydrates may be used or anhydrous one may be used for the present invention.

The metal oxide is obtained by reacting the metal or compound with hydrogen peroxide. As hydrogen peroxide, an aqueous solution is usually used. A solution of hydrogen peroxide in an organic solvent may be used and it is preferred to use the aqueous hydrogen peroxide solution from the viewpoint of easier handling. The concentration of hydrogen peroxide in the aqueous hydrogen peroxide solution or in the solution of hydrogen peroxide in the organic solvent is not particularly limited, but in view of volume efficacy and safety, the practical concentration is 1 to 60% by weight. As the aqueous hydrogen peroxide solution, a commercially available one is usually used as it is, or if necessary, it may be used after adjusting the concentration by dilution or concentration. The solution of hydrogen peroxide in the organic solvent can be prepared, for example, by extracting the aqueous hydrogen peroxide solution with the organic solvent, or distilling the solution in the presence of the organic solvent.

The amount of hydrogen peroxide to be used is usually 3 moles or more, preferably 5 moles or more relative to 1 mole of the metal or compound, and the upper limit thereof is not particularly defined.

The reaction of the metal or compound with hydrogen peroxide is usually carried out in an aqueous solution. The reaction may be carried out in an organic solvent such as an ether solvent such as diethyl ether, methyl tert-butyl ether and tetrahydrofuran, an ester solvent such as ethyl acetate, an alcohol solvent such as methanol, ethanol and tert-butanol, a nitrile solvent such as acetonitrile and propionitrile, or in a mixture of the organic solvent and water.

The reaction of the metal or compound with hydrogen peroxide is usually conducted by contacting both of them. In order to improve efficacy of contact between the metal or compound, and hydrogen peroxide, the reaction is preferably carried out with stirring so as to sufficiently disperse the metal or compound in a solution for preparing the metal oxide. The reaction temperature is usually −10 to 100° C.

By reacting the metal or compound with hydrogen peroxide in water, in the organic solvent, or in the mixed solvent of water and the organic solvent, all or a part of the metal or compound is dissolved, whereby, a homogeneous solution or slurry containing the metal oxide can be obtained. The metal oxide may be isolated from the homogeneous solution or slurry, for example, by concentration or filtration followed to preparing a metal-containing silicate, and the homogeneous solution or slurry may be used as it is for preparing the metal-containing silicate.

As the silicon compound, a tetraalkoxysilane such as tetramethoxysilane, tetraethoxysilane and tetraisopropoxysilane is usually used. The silicon compound is usually used in such an amount that silicon atoms are 4 moles or more relative to 1 mole of the metal atom of the above-mentioned metal oxide, and the upper limit thereof is not particularly defined.

Examples of the organic template include an alkylamine, a quaternary ammonium salt and a nonionic surfactant, and the alkylamine and the quaternary ammonium salt are preferable.

Examples of the alkylamine include a primary amine wherein a hydrogen atom of ammonia is substituted with an alkyl group having 8 to 20 carbon atoms such as octylamine, nonylamine, decylamine, undecylamine, dodecylamine, tridecylamine, tetradecylamine and eicosylamine; a secondary amine wherein one of hydrogen atoms of the amino group of the above-mentioned primary amine is substituted with a lower alkyl group having 1 to 6 carbon atoms such as a methyl group; and a tertiary amine wherein a hydrogen atoms of the amino group of the above-mentioned secondary amine is substituted with a lower alkyl group having 1 to 6 carbon atoms, and the primary amine is preferable.

As the quaternary ammonium salt, those consisting of a quaternary ammonium ion wherein four hydrogen atoms of the ammonium ion ($NH_4^+$) are substituted with same or different four alkyl groups having 1 to 18 carbon atoms and an anion such as a hydroxide ion, a chloride ion and a bromide ion are exemplified. Specific examples thereof include a quaternary ammonium hydroxide salt such as tetraethylammonium hydroxide, tetrapropylammonium hydroxide, tetrabutylammonium hydroxide and trimethyloctylammonium hydroxide; a quaternary ammonium chloride salt such as tetraethylammonium chloride, tetrapropylammonium chloride, tetrabutylammonium chloride and trimethyloctylammonium chloride; and a quaternary ammonium bromide salt such as tetraethylammonium bromide, tetrapropylammonium bromide, tetrabutylammonium bromide and trimethyloctylammonium bromide, and the quaternary ammonium hydroxide is preferable.

Examples of the nonionic surfactant include polyethylene glycol.

The organic template may be used as it is and by mixing with water or a hydrophilic solvent described below. The amount of the organic template to be used is usually 0.03 to 1 mole relative to 1 mole of the silicon compound.

The reaction of the above-mentioned metal oxide with the silicon compound in the presence of the organic template is usually conducted by mixing three components in the presence of a solvent. Examples of the solvent include water, the hydrophilic solvent and a mixture thereof, and water and mixed solvent of water and the hydrophilic solvent are preferable. Examples of the hydrophilic solvent include a hydrophilic alcohol solvent such as methanol, ethanol and isopropanol; a hydrophilic nitrile solvent such as acetnitrile; and a hydrophilic ether solvent such as dioxane, and the hydrophilic alcohol solvent is preferable, and methanol and ethanol are more preferable. The amount of the solvent to be used is usually 1 to 1000 parts by weight relative to 1 part by weight of the organic template.

The reaction temperature is usually 0 to 200° C.

After completion of the reaction, for example, the metal-containing silicate can be produced by separating the reaction product by filtration from the reaction liquid followed by washing or calcining the separated reaction product. In case of washing the separated reaction product, examples of the washing solvent include an alcohol solvent such as methanol and ethanol, and water. The amount thereof to be used is not particularly limited. In the case of calcining the separated reaction product, the calcination temperature is usually 300 to 700° C., preferably 500 to 600° C., and the calcination time is usually 0.5 to 20 hours. The separated reaction product may be calcinated after washing.

The metal-containing silicate thus obtained usually has pores of which the average micropore diameter is 4 to 100 Å (calculated by BHJ method based on the result measured by the nitrogen adsorption method) and the specific surface area thereof is usually 100 m$^2$/g or more (calculated by BET multipoint method ($p/p_0$=0.1) based on the result measured by the nitrogen adsorption method).

Next, the reaction of 1,2-epoxy-3-butene and water using the metal-containing silicate will be illustrated.

The amount of the metal-containing silicate to be used is usually 0.001 part by weight or more relative to 1 part by weight of 1,2-epoxy-3-butene. There is no specific upper limit and it is practically 5 parts by weight or less per 1 part by weight of 1,2-epoxy-3-butene considering economical viewpoint.

The amount of water to be used is usually 1 mole or more relative to 1 mole of 1,2-epoxy-3-butene. There is no specific upper limit and large excess amount thereof, for example, 500 moles relative to 1 mole of 1,2-epoxy-3-butene, may be used also to serve as the solvent.

The reaction of 1,2-epoxy-3-butene and water is usually conducted by mixing 1,2-epoxy-3-butene, water and the metal-containing silicate in the absence of a solvent or with using water as the solvent, and the mixing order is not particularly limited. The reaction may be carried out in the presence of an organic solvent. Examples of the organic solvent include an ether solvent such as diethyl ether, methyl tert-butyl ether and tetrahydrofuran; an ester solvent such as ethyl acetate; a tertiary alcohol solvent such as tert-butanol; and a nitrile solvent such as acetonitrile and propionitrile. These solvents may be used alone or in a form of a mixture. The amount of the organic solvent to be used is not particularly limited, and it is practically 100 parts by weight or less per 1 part by weight of 1,2-epoxy-3-butene considering volume efficacy.

The reaction is usually conducted under ordinary pressure conditions and may be conducted under reduced pressure conditions or pressurized conditions. The reaction temperature is usually –20 to 100° C., preferably 0 to 100° C.

The progress of the reaction can be confirmed by a conventional analytical means such as gas chromatography, high performance liquid chromatography, thin layer chromatography, nuclear magnetic resonance spectrum analysis and infrared adsorption spectrum analysis.

After completion of the reaction, 3-butene-1,2-diol can be isolated by concentrating a filtrate obtained by filtering off the metal-containing silicate. 3-Butene-1,2-diol can be also isolated by, if necessary, adding water and/or a water-insoluble organic solvent to the above-mentioned filtrate, followed by extracting to obtain an organic layer containing 3-butene-1, 2-diol and concentrating the organic layer as it is or after washing with water or an alkaline water, if necessary.

3-Butene-1,2-diol thus obtained can be used in the step (B) described below as it is or after further purifying by conventional purification means such as distillation and column chromatography. 3-Butene-1,2-diol may be used as a solution such as the above-mentioned filtrate or organic layer without isolating 3-butene-1,2-diol.

Next, the step (B): step of reacting 3-butene-1,2-diol with methanethiol to obtain 4-(methylthio)butane-1,2-diol will be illustrated.

As methanethiol, commercially available one may be used and one produced from methanol and hydrogen sulfide. Gaseous methanethiol may be used and liquid methanethiol may be used. Liquid methanethiol can be prepared, for example, by a method comprising bringing gaseous methanethiol into a container cooled below the boiling point thereof (6° C.) to condense it.

The amount of methanethiol to be used is usually 1 mole or more relative to 1 mole of 3-butene-1,2-diol. There is no upper limit particularly and considering economical viewpoint, the amount thereof is practically 10 moles or less relative to 1 mole of 3-butene-1,2-diol.

The reaction of 3-butene-1,2-diol and methanethiol is usually carried out in the absence of a solvent, and the reaction may be carried out in the presence of a solvent. The solvent is not particularly limited in so far as it does not prevent the reaction. Examples thereof include water; a hydrocarbon solvent such as hexane, heptane and toluene; a halogenated hydrocarbon solvent such as chlorobenzene and chloroform; an ether solvent such as diethyl ether, methyl tert-butyl ether and tetrahydrofuran; an ester solvent such as ethyl acetate; a tertiary alcohol solvent such as tert-butanol; and a nitrile solvent such as acetonitrile and propionitrile. They may be used alone or in a form of a mixture. The amount thereof to be used is not particularly limited, and it is practically 100 parts by weight or less per 1 part by weight of 3-butene-1,2-diol considering volume efficacy.

The reaction is usually conducted under ordinary pressure conditions or pressurized conditions, and may be conducted under reduced pressure conditions.

The reaction of 3-butene-1,2-diol and methanethiol is preferably conducted in the presence of a catalyst. Examples of the catalyst include known catalysts such as an organic peroxide and a boron compound. In the case of using the known catalyst such as the organic peroxide and the boron compound, the reaction can be conducted according to methods described in J. of Agricultural and Food Chemistry, 23, 1137 (1975) and EP 1260500 A.

As the catalyst of the present step (B), an azo compound can be also used. In the present step (B), the azo compound is preferably used as the catalyst. Herein, the azo compound means a compound which has an azo bond (—N=N—) within the molecule and of which decomposition temperature is below 250° C. Examples thereof include an azonitrile compound such as 2,2'-azobisisobutyronitrile, 2,2'-azobis(2,4-dimethylvaleronitrile), 2,2'-azobis(2-methylbutyronitrile), 1,1'-azobis(cyclohexane-1-carbonitrile), 4,4'-azobis-4-cyanopentanoic acid, 2-phenylazo-2,4-dimethyl-4-methoxyvaleronitrile and 2-cyano-2-propylazoformamide; an azoester compound such as azobisisobutanol diacetate, methyl azobisisobutyrate and ethyl azobisisobutyrate; an azoamidine compound such as 2,2'-azobis(2-amidinopropane) dihydrochloride; an azoimidazoline compound such as 2,2'-azobis[2-(2-imidazolin-2-yl)propane]; an azoamide compound such as 1,1'-azobisformamide, 1,1'-azobis(N-methylformamide) and 1,1'-azobis(N,N-dimethylformamide); and an azoalkyl compound such as azo-tert-butane. Preferred are the azonitrile compound, the azoester compound, the azoamidine compound and the azoimidazoline compound. The commercially available azo compound is usually used.

The amount of the azo compound to be used is usually 0.001 mole or more relative to 1 mole of 3-butene-1,2-diol. There is no specific upper limit and it is practically 0.2 mole or less relative to 1 mole of 3-butene-1,2-diol considering economical viewpoint.

The reaction temperature in the case of using the azo compound as the catalyst differs depending on kinds of the azo compound to be used and the amount thereof, and when the reaction temperature is too low, the reaction hardly proceeds and, when the reaction temperature is too high, side reaction such as polymerization of 3-butene-1,2-diol and the product may proceed. Therefore, the reaction is usually conducted in the range of −10 to 100° C., preferably of 0 to 50° C.

As the catalyst of the present step (B), a nitrogen-containing aromatic compound and an aliphatic carboxylic acid compound can be also used. In the present step (B), the nitrogen-containing aromatic compound and the aliphatic carboxylic acid compound are also preferably used as the catalyst.

The nitrogen-containing aromatic compound may be a monocyclic or condensed ring C3-C20 heteroaromatic compound in which at least one of atoms constituting the aromatic ring is a nitrogen atom. One or two or more of hydrogen atoms constituting the above-mentioned aromatic ring may be replaced with a substituent or substituents. Examples of the substituent include a halogen atom such as a fluorine, chlorine and bromine atom; a C1-C4 alkyl group such as a methyl, ethyl, n-propyl, isopropyl, n-butyl, isobutyl, sec-butyl and tert-butyl group; a C1-C4 alkoxy group such as a methoxy, ethoxy, n-propoxy, isopropoxy, n-butoxy, isbbutoxy, sec-butoxy and tert-butoxy group; a C2-C5 alkoxycarbonyl group such as a methoxycarbonyl, ethoxycarbonyl, n-propoxycarbonyl, isopropoxycarbonyl, n-butoxycarbonyl, and tert-butoxycarbonyl group; an amino group; and a carbamoyl group.

Examples of the nitrogen-containing aromatic compound include pyridine, piperidine, pyrazine, imidazole, benzimidazole, phenathroline, oxazole, thiazole, quinoline, isoquinoline, 2-methylpyridine, 3-methylpyridine, 4-methylpyridine, 2-chloropyridine, 3-chloropyridine, 4-chloropyridine, 2,3,5-collidine, 2,4,6-collidine, nicotinamide, methyl nicotinate, N-methylimidazole and 2-chloroquinopline. Among them, a pyridine compound which may have a substituent or substituents such as pyridine, 2-methylpyridine, 3-methylpyridine, 4-methylpyridine, 2-chloropyridine, 3-chloropyridine, 4-chloropyridine, 2,3,5-collidine, 2,4,6-collidine, nicotinamide and methyl nicotinate is preferable. As the nitrogen-containing aromatic compound, commercially available one is usually used.

The amount of the nitrogen-containing aromatic compound to be used is usually 0.001 mole or more relative to 1 mole of 3-butene-1,2-diol. There is no specific upper limit and it is practically 1 mole or less relative to 1 mole of 3-butene-1,2-diol considering economical viewpoint.

The aliphatic carboxylic acid may be a C1-C20 aliphatic compound having at least one carboxyl group. Examples thereof include formic acid, acetic acid, propionic acid, butanoic acid, pentanoic acid, hexanoic acid, oxalic acid, lactic acid, succinic acid and adipic acid. As the aliphatic carboxylic acid, commercially available one is usually used.

The amount of the aliphatic carboxylic acid compound to be used is usually 0.3 to 10 moles relative to 1 mole of the nitrogen-containing aromatic compound.

The nitrogen-containing aromatic compound and the aliphatic carboxylic acid compound may be previously mixed.

The reaction of 3-butene-1,2-diol and methanethiol is usually conducted by mixing the catalyst, 3-butene-1,2-diol and methanethiol, and the mixing order is not particularly limited. When the reaction is conducted under ordinary pressure conditions, the reaction is usually conducted by a method comprising adjusting a mixture of the catalyst and 3-butene-1,2-diol at a given temperature and blowing gaseous methanethiol into them. When the reaction is conducted under pressurized conditions, the reaction is conducted, for example, by a method comprising adding the catalyst and 3-butene-1,2-diol into a container capable of sealing such as autoclave, sealing the container and pressing gaseous methanethiol into it at a given temperature, and a method comprising adding the catalyst, 3-butene-1,2-diol and liquid methanethiol into the above-mentioned sealing container, sealing the container and adjusting at a given temperature. In the case of mixing 3-butene-1,2-diol, methanethiol and the catalyst followed by adjusting at a given temperature to effect reaction or in the case of mixing 3-butene-1,2-diol with methanethiol followed by adding the catalyst thereto to effect reaction, the amount of methanethiol in the mixture containing 3-butene-1,2-diol and methanethiol is preferably 4 moles or less relative to 1 mole of 3-butene-1,2-diol in order to start the reaction smoothly.

The progress of the reaction can be confirmed by a conventional analytical means such as gas chromatography, high performance liquid chromatography, thin layer chromatography, nuclear magnetic resonance spectrum analysis and infrared adsorption spectrum analysis.

When an lipophilic catalyst is used as the catalyst, after completion of the reaction, for example, 4-(methylthio)butane-1,2-diol can be isolated by removing methanethiol remained from the reaction mixture, and then, if necessary, adding water or an apolar solvent thereto, followed by extracting and concentrating the obtained aqueous layer containing 4-(methylthio)butane-1,2-diol. When a hypophilic catalyst is used as the catalyst, for example, 4-(methylthio)butane-1,2-diol can be isolated by removing methanethiol remained from the reaction mixture, and then, if necessary, adding water or a water-insoluble organic solvent thereto, followed by extracting and concentrating the obtained organic layer containing 4-(methylthio)butane-1,2-diol. Examples of the method for removing methanethiol remained from the reaction mixture include a method comprising concentrating the reaction mixture and a method comprising blowing an inert gas such as nitrogen gas into the reaction mixture. Examples of the apolar solvent include a hydrocarbon solvent such as hexane, heptane, toluene and xylene, and the amount thereof to be used is not particularly limited. Examples of the water-insoluble organic solvent include an ester solvent such as ethyl acetate and an ether solvent such as methyl tert-butyl ether besides the above-mentioned hydrocarbon solvent, and the amount thereof to be used is not particularly limited.

When the nitrogen-containing aromatic compound and the aliphatic carboxylic acid compound are used as the catalyst, after completion of the reaction, for example, 4-(methylthio) butane-1,2-diol can be isolated by removing methanethiol remained from the reaction mixture, and then, if necessary, adding water-insoluble organic solvent thereto, followed by extracting, washing the obtained organic layer containing 4-(methylthio)butane-1,2-diol with water, an acidic water and/or an alkaline water and concentrating thereof.

4-(Methylthio)butane-1,2-diol obtained can be used in the step (C) described below as it is or after further purifying by conventional purification means such as distillation and column chromatography. 4-(Methylthio)butane-1,2-diol may be used as a solution such as the above-mentioned organic layer without isolating 4-(methylthio)butane-1,2-diol.

Finally, the step (C): step of oxidizing 4-(methylthio)butane-1,2-diol to obtain 2-hydroxy-4-(methylthio)butyric acid will be illustrated.

In the present invention, the oxidation of the primary alcohol moiety within molecule of 4-(methylthio)butane-1,2-diol generally proceeds in priority to the oxidation of the secondary alcohol moiety and sulfide moiety.

Examples of the method for oxidizing 4-(methylthio)butane-1,2-diol to obtain 2-hydroxy-4-(methylthio)butyric acid include a method comprising conducting Swern oxidation of 4-(methylthio)butane-1,2-diol followed by oxidizing with silver nitrate and a method comprising bringing 4-(methylthio)butane-1,2-diol into contact with a microbial cell having an ability to convert 4-(methylthio)butane-1,2-diol into 2-hydroxy-4-(methylthio)butyric acid or a treated material thereof. Preferable example is the method comprising bringing 4-(methylthio)butane-1,2-diol into contact with a microbial cell having an ability to convert 4-(methylthio)butane-1, 2-diol into 2-hydroxy-4-(methylthio)butyric acid or a treated material thereof.

The method comprising conducting Swern oxidation of 4-(methylthio)butane-1,2-diol followed by oxidizing with silver nitrate can be conducted, for example, according to the method described in Tetrahedron, 48, 6043 (1992).

The method comprising bringing 4-(methylthio)butane-1, 2-diol into contact with a microbial cell having an ability to convert 4-(methylthio)butane-1,2-diol into 2-hydroxy-4-(methylthio)butyric acid or a treated material thereof will be illustrated.

Examples of the microbial cell having an ability to convert 4-(methylthio)butane-1,2-diol into 2-hydroxy-4-(methylthio)butyric acid or a treated material thereof include microbial cell or a treated material thereof such as microorganisms belonging to genus *Alcaligenes* such as *Alcaligenes faecalis, Alcaligenes denitrificans, Alcaligenes eutrophus, Alcaligenes* sp. and *Alcaligenes xylosoxydans*; microorganisms belonging to genus *Bacillus* such as *Bacillus alvei, Bacillus badius, Bacillus brevis, Bacillus cereus, Bacillus circulans, Bacillus coagulans, Bacillus firmus, Bacillus lentus, Bacillus licheniformis, Bacillus macerans, Bacillus megaterium, Bacillus moritai, Bacillus mycoides, Bacillus polymyxa, Bacillus pumilus, Bacillus sphaericus, Bacillus subtilis, Bacillus thuringenesis* and *Bacillus validus*;

microorganisms belonging to genus *Pseudomonas* such as *Pseudomonas auricularis, Pseudomonas azotoformans, Pseudomonas caryophylli, Pseudomonas chlororaphis, Pseudomonas denitrificans, Pseudomonas diminta, Pseudomonas fluorescens, Pseudomonas fragi, Pseudomonas fulva, Pseudomonas mendocina, Pseudomonas mutabilis, Pseudomonas nitroreducens, Pseudomonas oleovorans, Pseudomonas ovalis, Pseudomonas oxalaticus, Pseudomonas plantarii, Pseudomonas pseudoalcaligenes, Pseudomonas putida, Pseudomonas putrefaciens, Pseudomonas riboflavina, Pseudomonas* sp., *Pseudomonas straminea, Pseudomonas synxantha, Pseudomonas syringae, Pseudomonas tabaci, Pseudomonas taetrolens* and *Pseudomonas vesicularis*;

microorganisms belonging to genus *Rhodobacter* such as *Rhodobacter sphaeroides*; and microorganisms belonging to genus *Rhodococcus* such as *Rhodococcus erythropolis, Rhodococcus groberulus, Rhodococcus rhodochrous* and *Rhodococcus* sp.

Typically examples thereof include microbial cell or a treated material thereof such as *Alcaligenes faecalis* IFO13111t, *Alcaligenes denitrificans* JCM5490, *Alcaligenes eutrophus* ATCC43123, *Alcaligenes* sp. IFO14130, *Alcaligenes xylosoxydans* IF015125t, *Bacillus alvei* IFO3343 t, *Bacillus badius* ATCC14574t, *Bacillus brevis* IFO12334, *Bacillus cereus* JCM2503t, *Bacillus circulans* ATCC13403, *Bacillus coagulans* JCM2257t, *Bacillus firmus* JCM2512t, *Bacillus lentus* JCM2511t, *Bacillus licheniformis* IFO12195, *Bacillus macerans* JCM2500t, *Bacillus megaterium* IFO12108, *Bacillus moritai* ATCC21282, *Bacillus mycoides* IFO3039, *Bacillus polymyxa* IFO3020, *Bacillus pumilus* IFO12092t, *Bacillus sphaericus* IFO3341, *Bacillus subtilis* JCM1465t, *Bacillus thuringenesis* ATCC13366, *Bacillus validus* IFO13635, *Pseudomonas auricularis* IFO13334t, *Pseudomonas azotoformans* JCM2777t, *Pseudomonas caryophylli* IFO13591, *Pseudomonas chlororaphis* IFO3121t, *Pseudomonas denitrificans* IAM1923, *Pseudomonas diminta* JCM2788t, *Pseudomonas fluorescens* IFO14160t, *Pseudomonas fragi* IFO3458t, *Pseudomonas fulva* JCM2780t, *Pseudomonas mendocina* IFO14162, *Pseudomonas mutabilis* ATCC31014, *Pseudomonas nitroreducens* JCM2782t, *Pseudomonas oleovorans* IFO135835, *Pseudomonas ovalis* IFO12688, *Pseudomonas oxalaticus* IFO13593t, *Pseudomonas plantarii* JCM5492t, *Pseudomonas pseudoalcaligenes* JCM5968t, *Pseudomonas putida* IFO3738, *Pseudomonas putida* IAM1002, *Pseudomonas putida* IAM1090, *Pseudomonas putida* IAM1236, *Pseudomonas putida* ATCC39213, *Pseudomonas putrefaciens* IFO3910, *Pseudomonas riboflavina* IFO13584t, *Pseudomonas* sp. ATCC53617, *Pseudomonas straminea* JCM2783t, *Pseudomonas synxantha* IFO3913t, *Pseudomonas syringae* IFO14055, *Pseudomonas tabaci* IFO3508, *Pseudomonas taetrolens* IFO3460, *Pseudomonas vesicularis* JCM1477t, *Rhodobacter sphaeroides* ATCC17023, *Rhodococcus erythropolis* IFO12320, *Rhodococcus groberulus* ATCC15610, *Rhodococcus rhodochrous* JCM3202t, *Rhodococcus rhodochrous* ATCC15610 and *Rhodococcus* sp. ATCC19148.

As the microorganisms, at least one kind of microorganisms selected from genus *Alcaligenes*, genus *Bacillus*, genus *Pseudomonas*, genus *Rhodobacter* and genus *Rhodococcus* is preferable, at least one kind of microorganisms selected from genus *Bacillus*, genus *Pseudomonas* and genus *Rhodococcus* is more preferable, at least one kind of microorganisms selected from genus *Pseudomonas* and genus *Rhodococcus* is furthermore preferable, and microorganism belonging to genus *Rhodococcus* is especially preferable.

The microorganism can be cultured using culturing mediums for culturing various microorganisms accordingly containing carbon sources, nitrogen sources, organic salts or inorganic salts. Examples of the carbon source containing in the culturing mediums include glucose, sucrose, glycerol, starch, organic acids and molasses. Examples of the nitrogen source include yeast extract, meat extract, peptone, casamino acids, wheat germ extract, soy bean powder, corn steep liquor, cotton seed powder, dry yeast, ammonium sulfate and sodium nitrate. Examples of the salt of organic or inorganic acids include sodium chloride, potassium chloride, sodium carbonate, mono-potassium phosphate, di-potassium phosphate, calcium carbonate, ammonium acetate, magnesium sulfate, copper sulfate, zinc sulfate, ferrous sulfate and cobalt chloride.

Examples of the method for culturing include a solid culturing and liquid culturing (test tube culturing, flask culturing, Jar Fermenter culturing).

The culturing temperature and pH of the culturing liquid are not particularly limited as far as in the range wherein a microorganism grows, and the culturing temperature is usually about 15 to 40° C., and the pH of the culturing liquid is usually about 4 to 8. The culturing time can be accordingly selected depending on the culturing conditions and it is usually about 1 to 10 days.

The microbial cell can be used as it is. Examples of the method of using the fungus of the microbial cell as it is include (1) method comprising using the culturing liquid as it is and (2) method comprising correcting the cell by centrifugal separation of the culturing liquid and using the fungus corrected (the wet cell after washing with buffer liquid or water, if necessary).

The treated materials thereof can be used. Examples of the treated materials include those obtained by treating the cell obtained by culturing with an organic solvent (acetone, ethanol and the like), with freeze-drying or with an alkali, those obtained by disrupting physically or enzymatically, and crude enzyme separated and extracted from these materials. Further, the treated materials of the cell also include those obtained by subjecting the above-mentioned treatment followed by conducting immobilizing treatment according to the known method.

4-(Methylthio)butane-1,2-diol is oxidized to obtain 2-hydroxy-4-(methylthio)butyric acid by bringing the microbial cell or treated materials thereof into contact with 4-(methylthio)butane-1,2-diol.

The amount of the microbial cell or treated materials thereof to be used is an amount that the concentration of the microbial cell or treated materials thereof in the reaction liquid is usually 0.001 to 50% by weight, and preferably 0.01 to 20% by weight.

The reaction of the microbial cell or treated materials thereof and 4-(methylthio)butane-1,2-diol is usually carried out in the presence of water. As water, an aqueous buffering solution may be used and examples of the buffering agent used for the aqueous buffering solution include an alkali metal salt of phosphoric acid such as sodium phosphate and potassium phosphate; and an alkali metal salt of acetic acid such as sodium acetate and potassium acetate. The microbial cell or treated materials thereof may be reacted with 4-(methylthio)butane-1,2-diol in the presence of water and an organic solvent. The organic solvent may be a hydrophobic organic solvent or a hydrophilic organic solvent. Examples of the hydrophobic organic solvent include ester solvents such as ethyl formate, ethyl acetate, propyl acetate, butyl acetate, ethyl propionate and butyl propionate; hydrophobic alcohol solvents such as n-butyl alcohol, n-amyl alcohol and n-octyl alcohol; aromatic hydrocarbon solvents such as benzene, toluene and xylene; hydrophobic ether solvents such as diethyl ether, diisopropyl ether and methyl tert-butyl ether; halogenated hydrocarbon solvents such as chloroform and 1,2-dichloroethane; and a mixed solvent thereof. Examples of the hydrophilic organic solvent include hydrophilic alcohol solvents such as methanol and ethanol; hydrophilic ketone solvents such as acetone; hydrophilic ether solvents such as dimethoxyethane, tetrahydrofuran and dioxane; and a mixed solvent thereof.

The pH of reaction of the microbial cell or treated materials thereof and 4-(methylthio)butane-1,2-diol is usually in the range of 3 to 10, and the reaction temperature is usually 0 to 60° C. The reaction time is usually 0.5 hour to 10 days.

The concentration of 4-(methylthio)butane-1,2-diol in the reaction liquid is usually 50% (w/v) or less.

The reaction of the microbial cell or treated materials thereof and 4-(methylthio)butane-1,2-diol is usually conducted by mixing the both. The reaction may be conducted by adding 4-(methylthio)butane-1,2-diol continuously or successively to the reaction system.

If necessary, sugars such as glucose, sucrose and fructose, or a surfactant such as TritonX-100 and Tween60 may be added to the reaction system.

The ending point of the reaction can be confirmed by monitoring the amount of 4-(methylthio)butane-1,2-diol in the reaction liquid by liquid chromatography or gas chromatography.

After the completion of the reaction, 2-hydroxy-4-(methylthio)butyric acid can be isolated by conducting conventional aftertreatment of the reaction liquid such as extract treatment and concentration treatment. 2-Hydroxy-4-(methylthio)butyric acid obtained can be further purified by conventional purification means such as column chromatography and distillation.

EXAMPLES

The present invention will be further illustrated by Examples in detail below, but the present invention is not limited by these Examples.

Each of the specific surface area and the average micropore diameter of the metal-containing silicate obtained were measured at 150° C. under a degassed condition of $1.35 \times 10^{-5}$ Kg/cm$^{-2}$ (equivalent of 0.013 kPa) by the nitrogen adsorption method using Autosorb-6 manufactured by Quantachrome Instruments, and the specific surface area and the average micropore diameter thereof were calculated using BET multipoint method ($p/p_0$=0.1) and BHJ method respectively.

Reference Example 1

To a 500 mL flask equipped with a stirrer, 5 g of a tungsten metal powder and 25 g of ion-exchanged water were added, and an inner temperature was adjusted to 40° C. 15 g of a 60% by weight aqueous hydrogen peroxide solution was added dropwise thereto over 30 minutes, and then the mixture was maintained at the same temperature for 1 hour to obtain a solution containing tungsten oxide. To the solution containing tungsten oxide, 75 g of ion-exchanged water and 80 g of ethanol were added, and then 41.6 g of tetraethoxysilane was added dropwise thereto over 10 minutes. Further, 20 g of 40% by weight aqueous tetrabutylammonium hydroxide solution was added dropwise thereto at the same temperature over 10 minutes. Then, the mixture was cooled to an inner temperature of 25° C. and stirring was continued at the same temperature, and solid was precipitated in about 30 minutes to form slurry. After stirring and maintaining at the same temperature for 24 hours, solid was collected by filtration. Solid filtrated was washed twice with 100 g of ion-exchanged water, and then dried at 130° C. for 24 hours to obtain 38.0 g of the white solid. The white solid obtained was calcined at 550° C. for 6 hours to obtain 16.5 g of the white tungsten-containing silicate.

XRD spectrum: A broad peak having an apex at a d value of 3.77 Å is observed. A peak assignable to tungsten oxide is not observed.

IR spectrum (KBr)

$v_{max}$: 3478, 1638, 1078, 960, 806, 557 cm$^{-1}$

Elemental analysis value; W: 9.8%, Si: 39.5%

Specific surface area: 543 m$^2$/g, Average micropore diameter: 16 Å

Reference Example 2

To a 500 mL flask equipped with a stirrer, 5 g of a tungsten metal powder and 25 g of ion-exchanged water were added, and an inner temperature was adjusted to 40° C. 15 g of a 60% by weight aqueous hydrogen peroxide solution was added dropwise thereto over 30 minutes, and then the mixture was maintained at the same temperature for 2 hours to obtain a solution containing tungsten oxide. To the solution containing tungsten oxide, 75 g of ion-exchanged water and 80 g of ethanol were added, and then 41.6 g of tetraethoxysilane was added thereto at an inner temperature of 40° C. over 10 minutes. Further, 40 g of a 10% by weight tetrapropylammonium hydroxide solution was added dropwise thereto at the same temperature over 10 minutes. Then, the mixture was cooled to an inner temperature of 25° C. and stirring was continued at the same temperature. Solid was precipitated in about 30 minutes to form slurry. After stirring and maintaining at the same temperature for 24 hours, solid was collected by filtration. Solid filtrated was washed twice with 100 g of ion-exchanged water and dried at 130° C. for 24 hours to obtain 38.0 g of white solid. The white solid obtained was calcined at 550° C. for 6 hours to obtain 17.3 g of a white tungsten-containing silicate.

XRD spectrum: A broad peak having an apex at a d value of 3.76 Å is observed. A sharp peak assignable to tungsten oxide is slightly observed.

IR spectrum (KBr)

$v_{max}$: 3480, 1638, 1078, 956, 800 cm$^{-1}$

Elemental analysis value; W: 11.0%, Si: 31.4%

Specific surface area: 573 m$^2$/g, Average micropore diameter: 22 Å

Reference Example 3

To a 500 mL flask equipped with a stirrer, 2 g of a molybdenum metal powder and 25 g of ion-exchanged water were added, and an inner temperature was adjusted to 40° C. 15 g of a 60% by weight aqueous hydrogen peroxide solution was added dropwise thereto over 1 hour, and then the mixture was maintained at the same temperature for 1 hour to obtain a solution containing molybdenum oxide. To the solution containing molybdenum oxide, 75 g of ion-exchanged water and 80 g of ethanol were added, and then 41.6 g of tetraethoxysilane was added thereto at an inner temperature of 40° C. over 10 minutes. Further, 10 g of dodecylamine was added dropwise thereto at the same temperature over 10 minutes. Solid was immediately precipitated to form slurry. The mixture was cooled to an inner temperature of 25° C. and stirred and maintained for 24 hours, and then solid was collected by filtration. Solid filtrated was washed twice with 100 g of ion-exchanged water, dried at 110° C. for 6 hours and calcined at 550° C. for 6 hours to obtain 15.5 g of a white molybdenum-containing silicate.

XRD spectrum: A mixed spectrum of a broad peak having an apex at a d value of 3.8 Å and a sharp peak assignable to molybdenum oxide is observed.

IR spectrum (KBr)

$v_{max}$: 3470, 1640, 1090, 956, 915, 802 cm$^{-1}$

Elemental analysis value; Mo: 13.9%, Si: 32.4%

Specific surface area: 171 m$^2$/g, Average micropore diameter: 73 Å

It was confirmed that the white molybdenum-containing silicate obtained had molybdenum oxide from these results.

Reference Example 4

To a 500 mL flask equipped with a stirrer, 2.5 g of a molybdenum metal powder and 25 g of ion-exchanged water were added, and an inner temperature was adjusted to 40° C. 15 g of a 60% by weight aqueous hydrogen peroxide solution was added dropwise thereto over 1 hour, and then the mixture was maintained at the same temperature for 1 hour to obtain a solution containing molybdenum oxide. To the solution containing molybdenum oxide, 75 g of ion-exchanged water and 80 g of ethanol were added, and then 41.6 g of tetraethoxysilane was added thereto at an inner temperature of 40° C. over 10 minutes. Further, 20 g of a 40% by weight tetrabutylammonium hydroxide solution was added dropwise thereto over 10 minutes. Then, stirring was continued at the same temperature and solid was precipitated in about 15 minutes to form slurry. 200 g of ion-exchanged water was added to slurry. The mixture was cooled to an inner temperature of 25° C. and stirred and maintained at the same temperature for 24 hours. Then, solid was collected by filtration. Solid filtrated was washed twice with 100 g of ion-exchanged water, dried at 110° C. for 6 hours and calcined at 550° C. for 6 hours to obtain 15.9 g of a white molybdenum-containing silicate.

XRD spectrum: A broad peak having an apex at a d value of 3.79 Å is observed. A sharp peak assignable to tungsten oxide is not observed.

IR spectrum (KBr)

$v_{max}$: 3470, 1640, 1080, 956, 913, 796 cm$^{-1}$

Elemental analysis value; Mo: 5.22%, Si: 37.0%

Specific surface area: 649 m$^2$/g, Average micropore diameter: 22 Å

Reference Example 5

To a 500 mL flask equipped with a stirrer, 1.3 g of a vanadium metal powder and 25 g of ion-exchanged water were added, and an inner temperature was adjusted to 40° C. 15 g of a 30% by weight aqueous hydrogen peroxide solution was added dropwise thereto over 30 minutes, and then the mixture was maintained at the same temperature for 1 hour to obtain a solution containing vanadium oxide. To the solution containing vanadium oxide, 75 g of ion-exchanged water and 80 g of ethanol were added, and then 41.6 g of tetraethoxysilane was added thereto at an inner temperature of 40° C. over 10 minutes. Further, 40 g of a 40% by weight tetra-n-propylamine solution was added dropwise thereto over 10 minutes. Then, the mixture was cooled to an inner temperature of 25° C. and stirring was continued and solid was precipitated in about 30 minutes to form slurry. The slurry was stirred and maintained at the same temperature for 24 hours. Then, solid was collected by filtration. Solid filtrated was washed twice with 100 g of ion-exchanged water, dried at 130° C. for 8 hours and calcined at 550° C. for 6 hours to obtain 16.0 g of a brown vanadium-containing silicate.

XRD spectrum: A broad peak having an apex at a d value of 3.85 Å is observed. A sharp peak assignable to vanadium oxide is not observed.

IR spectrum (KBr)

$v_{max}$: 1050, 956, 794, 629 cm$^{-1}$

Elemental analysis value; V: 5.56%, Si: 36.1%

Specific surface area: 708 m$^2$/g, Average micropore diameter: 27 Å

Example 1

To a 50 mL flask equipped with a magnetic stirrer and a reflux condenser, 30 mg of the molybdenum-containing silicate obtained in the above-mentioned Reference Example 4, 310 mg of 1,2-epoxy-3-butene and 3 g of distilled water were added. The resultant mixture was stirred at an inner temperature of 25° C. for 5 hours to effect reaction. 10 g of tetrahydrofuran was added to the reaction liquid obtained to obtain a solution containing 3-butene-1,2-diol. The solution was analyzed by gas chromatography internal standard method to find the yield of 3-butene-1,2-diol was 93%.

Example 2

According to a similar manner as that of Example 1, the reaction was conducted except that the vanadium-containing silicate obtained in the above-mentioned Reference Example 5 was used in place of the molybdenum-containing silicate obtained in the above-mentioned Reference Example 4 and 300 mg of 1,2-epoxy-3-butene was used.

The yield of 3-butene-1,2-diol was 94%.

Example 3

According to a similar manner as that of Example 1, the reaction was conducted except that the molybdenum-containing silicate obtained in the above-mentioned Reference Example 3 was used in place of the molybdenum-containing silicate obtained in the above-mentioned Reference Example 4 and 330 mg of 1,2-epoxy-3-butene was used.

The yield of 3-butene-1,2-diol was 95%.

Example 4

According to a similar manner as that of Example 1, the reaction was conducted except that the tungsten-containing silicate obtained in the above-mentioned Reference Example 1 was used in place of the molybdenum-containing silicate obtained in the above-mentioned Reference Example 4.

The yield of 3-butene-1,2-diol was 81%.

Example 5

According to a similar manner as that of Example 1, the reaction was conducted except that the tungsten-containing silicate obtained in the above-mentioned Reference Example 2 was used in place of the molybdenum-containing silicate obtained in the above-mentioned Reference Example 4.

The yield of 3-butene-1,2-diol was 82%.

Example 6

Into a 50 mL flask equipped with a magnetic stirrer and a reflux condenser, 30 mg of the vanadium-containing silicate obtained in the above-mentioned Reference Example 5, 300 mg of 1,2-epoxy-3-butene and 3 g of distilled water were charged. The resultant mixture was stirred at an inner temperature of 25° C. for 5 hours to effect reaction. 10 g of tetrahydrofuran was added to the reaction liquid obtained, and then the vanadium-containing silicate was separated by decantation to obtain a solution containing 3-butene-1,2-diol. The solution was analyzed by gas chromatography internal standard method to find the yield of 3-butene-1,2-diol was 94%.

Example 7

Into a 50 mL flask equipped with a magnetic stirrer and a reflux condenser, all amount of the vanadium-containing silicate separated by decantation in the above-mentioned Example 6, 300 mg of 1,2-epoxy-3-butene and 3 g of distilled water were charged. The resultant mixture was stirred at an inner temperature of 25° C. for 5 hours to effect reaction. 10 g of tetrahydrofuran was added to the reaction liquid obtained to obtain a solution containing 3-butene-1,2-diol. The solution was analyzed by gas chromatography internal standard method to find the yield of 3-butene-1,2-diol was 87%.

Example 8

Into a 50 mL flask equipped with a magnetic stirrer and a reflux condenser, 30 mg of 85% phosphoric acid, 300 mg of 1,2-epoxy-3-butene and 3 g of distilled water were charged. The resultant mixture was stirred at an inner temperature of 5° C. for 5 hours to effect reaction. 10 g of tetrahydrofuran was added to the reaction liquid obtained to obtain a solution containing 3-butene-1,2-diol. The solution was analyzed by gas chromatography internal standard method to find the yield of 3-butene-1,2-diol was 92%.

Example 9

Into a 50 mL flask equipped with a magnetic stirrer and a reflux condenser, 30 mg of metaphosphoric acid, 300 mg of 1,2-epoxy-3-butene and 3 g of distilled water were charged. The resultant mixture was stirred at an inner temperature of 5° C. for 5 hours to effect reaction. 10 g of tetrahydrofuran was added to the reaction liquid obtained to obtain a solution containing 3-butene-1,2-diol. The solution was analyzed by gas chromatography internal standard method to find the yield of 3-butene-1,2-diol was 86%.

Example 10

To a 100 ml flask equipped with a magnetic stirrer, 880 mg of 3-butene-1,2-diol and 10 mg of 2,2'-azobisisobutyronitrile were added. Into the mixture obtained, gaseous methanethiol was blown at an inner temperature of 25° C. with stirring at a speed of about 10 to 20 mL/min. over 1 hour. The mixture was further stirred at the same temperature for 1 hour to effect reaction. After completion of the reaction, methanethiol remained was removed by blowing nitrogen into the reaction mixture, and 1245 mg of the oily matter containing 4-(methylthio)butane-1,2-diol was obtained. This oily matter was analyzed by gas chromatography area percentage method to find the yield of 4-(methylthio)butane-1,2-diol was 73%.

Example 11

To a 100 ml autoclave equipped with a magnetic stirrer, 1300 mg of 3-butene-1,2-diol and 20 mg of 2,2'-azobisisobutyronitrile were added. After cooling the mixture obtained at an inner temperature of 0° C., 1400 mg of liquid methanethiol was added thereto. The autoclave was sealed, and then the mixture was stirred at 30° C. for 2 hours to effect reaction. The pressure (gauge pressure) of internal autoclave at the point of starting the reaction was 2 kg/cm$^2$ (equivalent of 0.2 MPa) and the pressure (gauge pressure) of internal autoclave at the point of completion of the reaction was 1 kg/cm$^2$ (equivalent of 0.1 MPa). After completion of the reaction, methanethiol remained was removed by blowing nitrogen into the reaction mixture, and 1790 mg of the oily matter containing 4-(methylthio)butane-1,2-diol was obtained. This oily matter was analyzed by gas chromatography area percentage method to find the yield of 4-(methylthio)butane-1,2-diol was 67%.

Example 12

To a 100 ml autoclave equipped with a magnetic stirrer, 1300 mg of 3-butene-1,2-diol and 20 mg of azobisisobutyronitrile were added. After cooling the mixture obtained at an inner temperature of 0° C., 1400 mg of liquid methanethiol was added thereto. The autoclave was sealed, and then the mixture was stirred at 40° C. for 4 hours to effect reaction. The pressure (gauge pressure) of internal autoclave at the point of starting the reaction was 2.5 kg/cm$^2$ (equivalent of 0.25 MPa) and the pressure (gauge pressure) of internal autoclave at the point of completion of the reaction was 0.5 kg/cm$^2$ (equivalent of 0.05 MPa). After completion of the reaction, methanethiol remained was removed by blowing nitrogen into the reaction mixture, and 1990 mg of the oily matter containing 4-(methylthio)butane-1,2-diol was obtained. This oily matter was analyzed by gas chromatography area percentage method to find the yield of 4-(methylthio)butane-1,2-diol was 94%.

Example 13

To a 50 ml autoclave equipped with a magnetic stirrer, 2000 mg of 3-butene-1,2-diol and 20 mg of 2,2'-azobis[2-(2-imidazolin-2-yl)propane] were added. After cooling the mixture obtained at an inner temperature of 0° C., 1500 mg of liquid methanethiol was added thereto. The autoclave was sealed, and then the mixture was stirred at 40° C. for 4 hours to effect reaction. The pressure (gauge pressure) of internal autoclave at the point of starting the reaction was 2.5 kg/cm$^2$ (equivalent of 0.25 MPa) and the pressure (gauge pressure) of internal autoclave at the point of completion of the reaction was 0.5 kg/cm$^2$ (equivalent of 0.05 MPa). After completion of the reaction, methanethiol remained was removed by blowing nitrogen into the reaction mixture, and 10 g of ethyl acetate was added thereto to obtain the solution containing 4-(methylthio)butane-1,2-diol. The solution obtained was analyzed by gas chromatography internal standard method to find the yield of 4-(methylthio)butane-1,2-diol was 94%.

Example 14

According to a similar manner as that of Example 13, the solution containing 4-(methylthio)butane-1,2-diol was obtained except that methyl azobisisobutyrate was used in place of 2,2'-azobis[2-(2-imidazolin-2-yl)propane]. The solution obtained was analyzed by gas chromatography internal standard method to find the yield of 4-(methylthio)butane-1,2-diol was 98%.

Example 15

To a 50 ml autoclave equipped with a magnetic stirrer, 2000 mg of 3-butene-1,2-diol, 9 mg of pyridine and 14 mg of acetic acid were added. After cooling the mixture obtained at an inner temperature of 0° C., 1500 mg of liquid methanethiol was added thereto. The autoclave was sealed, and then the mixture was stirred at 40° C. for 4 hours to effect reaction. The pressure (gauge pressure) of internal autoclave at the point of starting the reaction was 2.5 kg/cm$^2$ (equivalent of 0.25 MPa) and the pressure (gauge pressure) of internal autoclave at the point of completion of the reaction was 0.5 kg/cm$^2$ (equivalent of 0.05 MPa). After completion of the reaction, the pressure was released to the ordinary pressure and methanethiol remained was removed by blowing nitrogen into the reaction mixture, and 10 g of ethyl acetate was added thereto. This solution was analyzed by gas chromatography internal standard method to find the yield of 4-(methylthio)butane-1,2-diol was 94%.

Example 16

The predetermined amount of water was added to the colorless oil obtained in Example 10 and insoluble matters was filtered off to prepare a 10% (w/v) aqueous 4-(methylthio)butane-1,2-diol solution.

5 ML of culturing medium after sterilization (those obtained by adding 20 g of glucose, 5 g of polypeptone, 3 g of yeast extract, 3 g of meat extract, 0.2 g of ammonium sulfate, 1 g of potassium dihydrogensulfate and 0.5 g of magnesium sulfate heptahydride thereto and adjusting pH thereof to 7.0) was added to the test tube, and various cells showed in Tables 1 to 4 were inoculated thereto. The shaking culture was conducted under an aerobic condition at 30° C. After completion of the culturing, the cells were separated by centrifugal separation to obtain a viable fungus. To the screw cap test tube, 2 mL of 0.1 M potassium phosphate buffer (pH 7) was added and the above-mentioned viable fungus was added thereto. 0.2 mL of the above-mentioned 10% (w/v) aqueous 4-(methylthio)butane-1,2-diol solution was added thereto and then, the mixture obtained was shaken at 30° C. for 2 to 3 days. After completion of the reaction, 1 mL of the reaction liquid was sampled. The cells were removed from the sampled liquid and the amount of 2-hydroxy-4-methylthiobutyric acid generated was analyzed by the liquid chromatography. The results obtained are shown in Tables 1 to 4. The formation rate (%) of 2-hydroxy-4-(methylthio)butyric acid was calculated based on 4-(methylthio)butane-1,2-diol.

The analytical condition of the liquid chromatography is followed.

Column: Cadenza CD-C18 (4.6 mmφ×15 cm, 3 µm) (manufactured by Imtakt Corporation)

Mobile phase: Liquid A 0.1% aqueous trifluoroacetic acid solution, Liquid B methanol Gradient Conditions:

0 to 10 minutes Liquid A/Liquid B=80/20 (constant)

10 to 20 minutes to Liquid A/Liquid B=50:50 over 10 minutes 20 to 30 minutes Liquid A/Liquid B=50:50 (constant)

30 to 30.1 minutes to Liquid A/Liquid B=80:20 over 0.1 minutes 30.1 to 50 minutes Liquid A/Liquid B=80:20 (constant)

Flow rate: 0.5 mL/min., column temperature: 40° C., Detection wavelength: 220 nm

TABLE 1

| Name of Strain | Formation rate of 2-hydroxy-4-(methylthio)butyric acid (%) |
|---|---|
| Alcaligenes faecalis IFO 13111t | 0.1 |
| Alcaligenes denitrificans JCM 5490 | 0.4 |
| Alcaligenes eutrophus ATCC 43123 | 0.1 |
| Alcaligenes faecalis IFO 12669 | 0.2 |
| Alcaligenes faecalis IFO 14479 | 0.1 |
| Alcaligenes faecalis JCM 5485t | 2.5 |
| Alcaligenes sp. IFO 14130 | 0.1 |
| Alcaligenes xylosoxydans IFO15125t denitrificans | 0.2 |
| Alcaligenes xylosoxydans IFO15126t xylosoxydans | 0.5 |
| Bacillus alvei IFO 3343t | 17.0 |
| Bacillus badius ATCC 14574t | 7.3 |
| Bacillus brevis IFO 12334 | 4.7 |
| Bacillus brevis JCM 2503t | 4.2 |
| Bacillus cereus JCM 2152t | 11.2 |
| Bacillus cereus var. juroi ATCC 21281 | 10.3 |
| Bacillus cereus var. mycoides IFO 3039 | 2.6 |
| Bacillus circulans ATCC 13403 | 1.2 |
| Bacillus circulans IFO 3329 | 2.8 |
| Bacillus circulans JCM 2504t | 1.4 |
| Bacillus coagulans JCM 2257t | 5.0 |
| Bacillus firmus JCM 2512t | 0.6 |
| Bacillus lentus JCM 2511t | 3.6 |
| Bacillus licheniformis ATCC 27811 | 2.0 |
| Bacillus licheniformis IFO 12195 | 1.8 |
| Bacillus licheniformis IFO 12195 | 1.3 |
| Bacillus licheniformis IFO 12197 | 12.9 |
| Bacillus licheniformis IFO 12200t | 1.3 |
| Bacillus macerans JCM 2500t | 1.5 |
| Bacillus megaterium IFO 12108 | 0.6 |
| Bacillus megaterium JCM 2506t | 1.2 |

TABLE 2

| Name of Strain | Formation rate of 2-hydroxy-4-(methylthio)butyric acid (%) |
|---|---|
| Bacillus moritai ATCC 21282 | 11.5 |
| Bacillus mycoides IFO 3039 | 6.0 |
| Bacillus polymyxa IFO 3020 | 3.5 |
| Bacillus polymyxa JCM 2507t | 2.8 |
| Bacillus pumilus IFO 12092t | 1.5 |
| Bacillus sphaericus IFO 3341 | 13.2 |
| Bacillus sphaericus IFO 3525 | 0.6 |
| Bacillus sphaericus IFO 3526 | 6.2 |
| Bacillus sphaericus IFO 3527 | 4.0 |
| Bacillus sphaericus IFO 3528 | 1.6 |
| Bacillus subtilis JCM 1465t | 10.8 |
| Bacillus subtilis ATCC 14593 | 1.7 |
| Bacillus subtilis ATCC15841 | 5.6 |
| Bacillus subtilis IFO 03026 | 2.8 |
| Bacillus subtilis IFO 03108 | 2.5 |
| Bacillus subtilis IFO 03134 | 2.8 |
| Bacillus subtilis IFO 3026 | 3.3 |
| Bacillus subtilis IFO 3037 | 2.7 |
| Bacillus subtilis IFO 3108 | 1.7 |
| Bacillus subtilis IFO 3134 | 1.5 |
| Bacillus thuringensis ATCC 13366 | 10.4 |
| Bacillus validus IFO 13635 | 3.8 |
| Pseudomonas auricularis IFO 13334t | 1.9 |
| Pseudomonas azotoformans JCM 2777t | 8.9 |
| Pseudomonas caryophylli IFO 13591 | 0.4 |
| Pseudomonas chlororaphis IFO 3521t | 1.1 |
| Pseudomonas chlororaphis IFO 3904t | 0.7 |
| Pseudomonas denitrificans IAM 1923 | 2.7 |
| Pseudomonas diminuta JCM 2788t | 38.9 |

TABLE 3

| Name of Strain | Formation rate of 2-hydroxy-4-(methylthio)butyric acid (%) |
|---|---|
| Pseudomonas fluorescens Biotype F ATCC 17513 | 7.6 |
| Pseudomonas fluorescens IFO 14160t | 0.3 |
| Pseudomonas fragi IAM12402 | 0.1 |
| Pseudomonas fragi IFO 3458t | 0.4 |
| Pseudomonas fulva JCM 2780t | 1.1 |
| Pseudomonas mendooina IFO 14162 | 34.1 |
| Pseudomonas mutabilis ATCC31014 | 13.5 |
| Pseudomonas nitroreducens JCM 2782t | 8.4 |
| Pseudomonas oleovorans IFO 13583t | 0.3 |
| Pseudomonas ovalis IFO 12688 | 1.4 |
| Pseudomonas oxalaticus IFO 13593t | 0.2 |
| Pseudomonas plantarii JCM 5492t | 1.3 |
| Pseudomonas pseudo Alcaligenes JCM 5968t | 36.2 |
| Pseudomonas putida ATCC 17428 | 1.5 |
| Pseudomonas putida ATCC 17484 | 9.9 |
| Pseudomonas putida ATCC39213 | 23.3 |
| Pseudomonas putida IAM 1002 | 20.5 |
| Pseudomonas putida IAM 1090 | 28.1 |
| Pseudomonas putida IAM 1094 | 1.0 |
| Pseudomonas putida IAM 1236 | 19.6 |
| Pseudomonas putida IFO 12996 | 5.6 |
| Pseudomonas putida IFO 13696 | 9.3 |
| Pseudomonas putida IFO 14164t | 41.2 |
| Pseudomonas putida IFO 14671 | 0.9 |
| Pseudomonas putida IFO 14796 | 1.0 |
| Pseudomonas putida IFO 3738 | 38.2 |
| Pseudomonas putida IFO12653 | 5.7 |
| Pseudomonas putida JCM 6156 | 1.5 |
| Pseudomonas putida JCM 6157 | 0.5 |
| Pseudomonas putida JCM 6158 | 1.2 |

TABLE 4

| Name of Strain | Formation rate of 2-hydroxy-4-(methylthio)butyric acid (%) |
|---|---|
| Pseudomonas putrefaciens IFO 3910 | 0.2 |
| Pseudomonas riboflavina IFO 13584t | 0.1 |
| Pseudomonas sp. ATCC 53617 | 4.4 |
| Pseudomonas straminea JCM 2783t | 1.0 |
| Pseudomonas synxantha IFO 3913t | 0.4 |
| Pseudomonas syringae subsp. syringae IFO14055 | 3.8 |
| Pseudomonas tabaci IFO 3508 | 1.7 |
| Pseudomonas taetrolens IFO 3460 | 0.3 |
| Pseudomonas vesicularis JCM 1477t | 8.4 |
| Rhodobacter sphaeroides ATCC 17023 | 3.0 |
| Rhodococcus erythropolis IFO 12320 | 21.7 |
| Rhodococcus globerulus ATCC 15076 | 22.7 |
| Rhodococcus rhodochrous ATCC 15610 | 58.9 |
| Rhodococcus rhodochrous ATCC 19067 | 16.0 |
| Rhodococcus rhodochrous ATCC 19149 | 14.6 |
| Rhodococcus rhodochrous ATCC 19150 | 12.3 |
| Rhodococcus rhodochrous ATCC 21197 | 2.7 |
| Rhodococcus rhodochrous ATCC 21199 | 7.9 |
| Rhodococcus rhodochrous JCM 3202t | 30.9 |
| Rhodococcus sp ATCC 19070 | 13.1 |
| Rhodococcus sp ATCC 19071 | 7.7 |
| Rhodococcus sp ATCC 19148 | 34.5 |

The invention claimed is:

1. A method for producing 2-hydroxy-4-(methylthio)butyric acid which comprises the following steps (A), (B) and (C):

Step (A): step of reacting 1,2-epoxy-3-butene with water to obtain 3-butene-1,2-diol, Step (B): step of reacting 3-butene-1,2-diol with methanethiol to obtain 4-(methylthio)butane-1,2-diol, Step (C): step of oxidizing 4-(methylthio)butane-1,2-diol to obtain 2-hydroxy-4-(methylthio)butyric acid.

2. The method according to claim 1, wherein the reaction is conducted in the presence of an acid in the step (A).

3. The method according to claim 2, wherein the acid is a silicate containing at least one element selected from a group 5 element and a group 6 element of the long periodic table as a constituent.

4. The method according to claim 3, wherein the silicate containing at least one element selected from a group 5 element and a group 6 element of the long periodic table is vanadium, tungsten or molybdenum.

5. The method according to claim 2, wherein the acid is a phosphoric acid compound.

6. The method according to claim 1, wherein 1,2-epoxy-3-butene is 1,2-epoxy-3-butene obtained by oxidizing butadiene in the step (A).

7. The method according to claim 1, wherein the reaction is conducted in the presence of a catalyst in the step (B).

8. The method according to claim 7, wherein the catalyst is an azo compound.

9. The method according to claim 8, wherein the azo compound is an azonitrile compound, an azoester compound, an azoamidine compound or an azoimidazoline compound.

10. The method according to claim 7, wherein the catalyst is a nitrogen-containing aromatic compound and an aliphatic carboxylic acid compound.

11. The method according to claim 1, wherein
4-(methylthio)butane-1,2-diol is oxidized by bringing 4-(methylthio)butane-1,2-diol into contact with a microbial cell having an ability to convert 4-(methylthio)butane-1,2-diol into 2-hydroxy-4-(methylthio) butyric acid or a treated material thereof in the step (C), wherein the microbial cell is at least one selected from the group consisting of genus *Alcaligenes*, genus *Bacillus*, genus *Pseudomonas*, genus *Rhodobacter* and genus *Rhodococcus*.

12. The method according to claim 11, wherein the microbial cell is at least one kind of microorganisms selected from the group consisting of *Alcaligenes faecalis, Alcaligenes denitrificans, Alcaligenes eutrophus, Alcaligenes sp., Alcaligenes xylosoxvdans, Bacillus alvei, Bacillus badius, Bacillus brevis, Bacillus cereus, Bacillus circulans, Bacillus coagulans, Bacillus firmus, Bacillus lentus, Bacillus licheniformis, Bacillus macerans, Bacillus megaterium, Bacillus moritai, Bacillus mycoides, Bacillus polymyxa, Bacillus pumilus, Bacillus sphaericus, Bacillus subtilis, Bacillus thuringenesis, Bacillus validus, Pseudomonas auricularis, Pseudomonas azotoformans, Pseudomonas caryophylli, Pseudomonas chlororaphis, Pseudomonas denitrificans, Pseudomonas diminuta, Pseudomonas fluorescens, Pseudomonas fragi, Pseudomonas fulva, Pseudomonas mendocina, Pseudomonas mutabilis, Pseudomonas nitroreducens, Pseudomonas oleovorans, Pseudomonas ovalis, Pseudomonas oxalaticus, Pseudomonas plantarii, Pseudomonas pseudoalcaligenes, Pseudomonas putida, Pseudomonas putrefaciens, Pseudomonas riboflavina, Pseudomonas sp., Pseudomonas straminea, Pseudamonas synxantha, Pseudomonas syringae, Pseudomonas tabaci, Pseudomonas taetrolens, Pseudomonas vesicularis, Rhodobacter sphaeroides, Rhodococcus erythropolis, Rhodococcus groberulus, Rhodococcus rhodochrous* and *Rhodococcus sp.*

* * * * *

UNITED STATES PATENT AND TRADEMARK OFFICE
CERTIFICATE OF CORRECTION

PATENT NO. : 7,632,664 B2
APPLICATION NO. : 11/665070
DATED : December 15, 2009
INVENTOR(S) : Koji Hagiya and Hiroyuki Asako Page 1 of 1

It is certified that error appears in the above-identified patent and that said Letters Patent is hereby corrected as shown below:

Title page insert the Foreign Application Priority Data item (30) to read:

--Oct. 14, 2004   (JP)................................2004-299654--

Signed and Sealed this

Sixteenth Day of February, 2010

David J. Kappos
*Director of the United States Patent and Trademark Office*